United States Patent [19]

Jaffe et al.

[11] 4,158,036
[45] Jun. 12, 1979

[54] FLUID BED HEAT RECOVERY APPARATUS

[75] Inventors: James Jaffe, Lake Hopatcong, N.J.;
Thomas J. O'Rourke, Grand Island;
Arthur S. Chu, Amherst, both of
N.Y.

[73] Assignee: Allied Chemical Corporation, Morris
Township, Morris County, N.J.

[21] Appl. No.: 792,749

[22] Filed: May 2, 1977

[51] Int. Cl.² .................. B01J 8/28; F28D 13/00
[52] U.S. Cl. ................................. 422/142; 165/104 F;
422/143; 422/145; 422/146; 422/197; 422/202;
422/311; 423/659; 423/DIG. 16; 432/15;
432/58
[58] Field of Search ................ 23/288 S, 288 M, 284;
423/DIG. 16, 659; 432/15, 58; 165/104 F

[56] References Cited
U.S. PATENT DOCUMENTS

| 2,532,756 | 12/1950 | Brunjes et al. ............... 23/288 M |
| 2,560,356 | 7/1951 | Liedholm ...................... 23/288 S X |
| 2,934,551 | 4/1960 | Stringer ........................ 23/288 S X |
| 2,989,544 | 6/1961 | Saunders et al. .............. 23/288 S X |
| 3,055,745 | 9/1962 | Drummond et al. ............. 23/288 S |
| 3,080,382 | 3/1963 | Rousseau ..................... 23/288 S X |
| 3,119,378 | 1/1964 | Marshall ....................... 23/288 S X |
| 3,151,944 | 10/1964 | Stevens et al. ................. 23/288 S |
| 3,224,869 | 12/1965 | Keith et al. ................... 23/288 S X |
| 3,482,946 | 12/1969 | Shirk ........................... 23/288 S X |
| 3,532,472 | 10/1970 | Foster .......................... 23/288 M |
| 3,783,528 | 1/1974 | Sheely ........................... 23/288 S X |
| 3,991,816 | 11/1976 | Klaren ......................... 23/288 S X |
| 4,039,290 | 8/1977 | Inada et al. .................. 23/288 S X |

Primary Examiner—Joseph Scovronek
Attorney, Agent, or Firm—Alan M. Doernberg; Jay P. Friedenson

[57] ABSTRACT

A fluid bed reactor including a first, upstream reaction zone having a fluidized bed of particles and a second, downstream heat recovery zone having a fluidized bed of particles. The reactor is designed adjacent the heat recovery zone to withdraw heat from the heat recovery zone at a temperature lower than the temperature in the reaction zone. In operation, the particles in the heat recovery zone cool and quench the effluent from the reaction zone so as to remove fines and volatile elutriates therefrom, rendering the effluent less corrosive and preventing back or side reactions.

3 Claims, 8 Drawing Figures

FLUID BED HEAT RECOVERY APPARATUS

BACKGROUND OF THE INVENTION

This invention relates to a heat recovery apparatus and method to recover heat from a fluid bed chemical reactor. In particular, the invention relates to the lowering of the temperature of the reaction product outflow from a fluidized reactor bed.

A wide variety of chemical processes are conducted in fluid beds. Included in such processes are chemical reactions, calcination and absorption. Examples of such processes are oxychlorination of ethylene with hydrogen chloride and air to produce ethylene dichloride, roasting of pyrites with air to produce sulfur dioxide, drying and/or calcining of phosphate rock, production and reduction of uranium hexafluoride, hydrofluorination, fluorination and oxidation of o-xylene to phthallic acid.

Conventionally, a reactor chamber is provided at the lower end with one or more inlets through which gaseous reactants, carriers and/or processing gaseous streams are introduced. A particulate material is supported by a grate or other support in the path of the gas flow. At sufficient gas velocity, the fluidization begins and a fluid bed is formed above the grate. Product gas flow from the fluid bed passes downstream, usually upward, frequently through a cyclone in which carried particles or elutriates are recovered.

In many such processes the fluid bed operates at a sufficiently high temperature, either because of preheating of the gases or because of an exothermic reaction, to recover heat in the reaction fluid bed. Such temperatures exceed 500° C. and frequently exceed 700° C. Devices are also sometimes provided outside the reactor to recover heat from the effluent, as in a waste-heat boiler. In such large boilers, high pressure steam over about 200 psi and generally over about 450 psi is generated. In many systems, the gas outflow passes through a heat exchanger in a countercurrent relation to a coolant, such as water. An economizer is sometimes used to preheat the water with the gaseous outflow from the waste heat boiler.

A waste heat boiler has distinct disadvantages with such systems. When an undesired side or back reaction can occur in the effluent, it is usually desirable to quickly quench the effluent, which is not done by a waste heat boiler. Secondly, many reaction product gases include highly corrosive components, particularly water and acids such as hydrochloric acid and hydrogen fluoride. Such components are frequently most corrosive at the elevated reaction temperatures, and will therefore attack metal and other surfaces in the cyclone or inlet portions to the waste heat boiler. Furthermore, the large waste heat boiler used is usually not designed to withstand the high pressures of some fluid bed reaction systems or to operate economically with many fluid bed reaction systems.

Moreover, there are many reactions in which the reaction gas outflow is below about 700° C., and particularly below about 500° C., and thus no high pressure steam could be economically recovered. Especially when undesired side or back reactions occur in the reaction product gas at reaction temperatures, the reaction product gas is usually quenched in ways that heat is not recovered in usable form.

Additionally, in reaction product gases containing both acids and water, it is most undesirable that the product gas cool to below the dew point of the water vapor. When this occurs, an aqueous acid solution is formed which may be more corrosive than the gaseous water vapor and acid. Most quenching systems have inadequate temperature control to prevent this condensation.

Finally, waste heat boilers do nothing to assist the cyclone in the recovery of particles from the fluid bed carried by the gas outflow. Instead, such materials as copper catalysts which begin to form a vapor at about 400° C. may travel past the cyclone and cause potential corrosion, contamination or pollution problems downstream from the cyclone.

It is known to recover heat from within a reaction bed in which an exothermic reaction is occurring. Materials such as liquid salts are conventionally passed in a heat exchanger tube or coil through the reaction fluid bed to recover heat at the reaction temperature and prevent the reaction bed from overheating. If the salt absorbs the heat at temperatures above about 350° C., high temperature steam may be generated outside the reactor by heat exchange contact with the liquid salt.

It is also known to provide chambers with multiple fluid beds. Particularly for calcining processes, the particulate material to be calcined is conventionally passed downward through a series of fluid beds being successively heated by a heating gas flow passing upward through the same fluid bed. A similar arrangement is provided in systems in which a solid particle, such as alumina, is reacted with a gaseous reactant, such as hydrogen fluoride, to produce a solid product, such as aluminum fluoride. An example of such a process is disclosed in U.S. Pat. No. 3,473,887.

U.S. Pat. No. 3,967,975 discloses a housing with an upper and lower chamber and series of connecting tubes therebetween, with a fluidizing gas fluidizing material in both chambers and the connecting tube. Heat transfer jackets are provided for each chamber and the tubes. The material forms a continuous fluidized bed in the tubes in the adjacent portions of each chamber, preventing the maintenance of any temperature differential therebetween.

U.S. Pat. No. 3,795,490 discloses an apparatus for thermal cracking of hydrocarbons including a lower heating and reaction tower (in which heated molten metal circulates), an intermediate transfer line portion and an upper quenching tower with quenching tubes. Fluidized sand particles occupy the intermediate transfer line portion, the adjacent portion of a lower tower down to the molten metal surface and the adjacent portion of the quenching tower up to above the quenching tubes. Although a temperature differential must be maintained between the molten metal and the quenching tubes, the continuous fluidized bed of sand particles would tend to conduct heat therebetween and increase the amount of heat input required for the molten catalyst, while reducing the effectiveness of the quenching tubes.

U.S. Pat. No. 3,307,921 discloses a reactor with multiple reaction-promoting catalyst beds in series and between each bed a heat exchanger section to withdraw heat from the reactor fluid as it passes from one stage to the next. In such a device, the only heat exchange surfaces are those of the heat exchanger, and the relatively large heat exchange surfaces of the particles are not utilized.

U.S. Pat. No. 2,779,777 discloses cooling coils immersed in particle beds. U.S. Pat. Nos. 2,622,970 and 2,926,143 disclose such coils immersed in a fluid bed of catalytic particles.

In none of the references is the high conductivity of fluidized particles utilized to quickly withdraw heat from the effluent from a hot reaction zone without simultaneously withdrawing heat from the reaction zone itself. The temperature differential required for efficient, rapid quenching of the reaction effluent and good waste heat utilization cannot be maintained if the fluidized particles can rapidly transfer heat out of the reaction bed into the zone through which the effluent must pass.

BRIEF DESCRIPTION OF THE INVENTION

The invention includes a reactor apparatus with a housing, an inlet for fluidizing gas and reactants and an outlet for the effluent from the reaction, having a first support means for supporting a first bed of fluidized particles in which a high temperature reaction may occur and a second support means downstream from the first support means and the first fluidized bed for supporting a second bed of fluidized particles. Means are provided to withdraw heat from the second bed of fluidized particles at a selected temperature less than the temperature of the high temperature reaction. The term "support means" is used herein to describe a device such as a grate which will support a fluidized bed under operating conditions. Such "support means" may, but need not necessarily, support the particles under static conditions.

The invention also includes a method for conducting a high temperature reaction in a fluid bed reactor including the steps of passing fluidized gas under pressure successively through a first and second support forming a first fluidized bed of particles above the first support and a second fluidized bed of particles above the second support, conducting a high temperature reaction in the first fluidized bed with the effluent therefrom passing to the second fluid bed and withdrawing heat from the particles of the second bed. The second fluid bed is maintained at a temperature lower than the reaction temperature in the first fluid bed.

In preferred forms, the second support means is designed to permit sufficiently large flows of particles between the first and second fluid beds to maintain an homogeneous composition therebetween, but a sufficiently small flow of particles for the desired temperature differential to be maintained between the first and second fluid beds. Also in some forms, heat is withdrawn from the second fluid bed at between about 150° C. and about 250° C. while the first fluid bed is maintained at at least about 350° C.

DETAILED DESCRIPTION OF THE INVENTION

The invention includes a fluid bed reactor apparatus with an upstream reactor zone and a downstream heat recovery zone, both including support means for fluidized particles when a fluidizing gas is passed through the reactor. Means are provided to withdraw heat from the fluidized particles in the heat recovery zone at a temperature lower than that in the reaction zone when the reaction zone is heated by the occurrence of an exothermic reaction or heating of the reactor zone from an external source. The heat recovery zone both recovers heat from and quenches the effluent from the reactor zone.

This basic system offers the following advantages: (1) the effluent from the reactor zone is rapidly quenched to lessen side or back reactions, including the explosive reactions, in the effluent, (2) the temperature of the effluent is lowered, often lowering its corrosiveness and (3) the rate of flow of gases beyond the heat recovery zone is lowered, because of gas law volume changes with decreased temperature, so as to decrease the amount of fines in the effluent from the reactor. This third property enhances the operation of a cyclone, which is frequently provided to remove fines from the effluent, by permitting operation on a smaller gas flow and reducing the particle content to be recovered.

A preferred mode of the invention is a reactor with a lower grate through which fluidized particles will not normally pass downward, and an upper grate with an aperture large enough to permit the interchange of particles between the lower reaction zone and the upper heat recovery zone.

The invention includes the method of operating such an apparatus to cause an exothermic or other high temperature reaction in the reaction zone and effectuate quenching and heat recovery in the heat recovery zone. In one preferred method the fluidized particles are generally identical in both zones and, with the above preferred apparatus, the interchange of particles permits the composition of the fluidized particles to remain substantially homogeneous. The interchange is sufficiently low, however, to maintain a desired temperature differential between the two zones so that the reaction zone is sufficiently high in temperature to carry out the reaction, and the heat recovery zone is sufficiently low to quench the reaction. Especially preferred are upper grates with a smaller number of relatively large apertures thereby preventing plugging of the upper grate. Such apertures are typically about 30 to about 200 times the size of the average particles in diameter.

It will be appreciated that the total effective cross-sectional void area of each grid, as compared to the total cross-section of the reactor at the grate, will be adjusted to determine desired fluid flow rates, bed heights and particle interchange rates.

When exothermic reactions occur in the reaction zone, with corrosive products in the effluent from the reaction zone, the upper heat recovery zone both quenches and renders less corrosive the effluent. When the particles in the reaction are catalytic particles with a volatile component which is elutriated, varied or carried off into the effluent at reaction temperatures, the volatile component is recovered in the heat recovery zone on particles at a lower temperature. Without the fluidized bed as a heat recovery zone, these volatile components, often corrosive, would adhere to the wall of the apparatus or pass downstream with the effluent. With the preferred apparatus, in which the upper grate permits the interchange of particles between the two fluidized beds during reaction, particles with the recovered volatile component can pass back downward into the reaction zone, causing a recycling of the volatile component during continued operation of the reactor.

The means provided to withdraw heat from the particles in the heat recovery zone could be, for example, a coil immersed in the particles of the upper bed connected to a source of relatively cool material such as water and an outlet for heated material such as steam. For some uses, even low pressure steam, recovered at between about 150° C. and about 250° C., may be generated, enhancing the quenching properties of the heat recovery zone. By maintaining a temperature above about 150° C., condensation of water vapor in the effluent is prevented. The means could also be a jacket around the exterior portion of the reactor of the heat recovery zone to withdraw heat from particles reaching the exterior of the zone. When it is not desired to recover heat from the heat recovery zone, but merely to quench the effluent from the reactor zone, the means could be an uninsulated region of the reactor wall adjacent the heat recovery zone.

One particularly suitable form of the invention for many chemical reactions is a multi-tube reactor in which similar reactants are fed into small, parallel reactor tubes, each provided with a reactor fluidized bed over a lower grate and a heat recovery fluidized bed over an upper grate, which may be the large apertured grate described above. In such a multi-tube reactor, the means for drawing heat can be an enclosed region contacting the portion of the exterior of each tube adjacent the heat recovery zone. A cooling fluid such as water can be circulated through the enclosed region generating, for example, low pressure steam from heat withdrawn from the heat recovery zone of each tube, and maintaining the temperature of the heat recovery zone substantially uniform. In many multi-tube reactors, the tubes need not extend the entire length of the reactor, but rather the reactor zones and the heat recovery zones may be contained in colinear tube segments, with larger mixing zones below, above and between the tube portions.

DESCRIPTION OF THE PREFERRED EMBODIMENTS

Simple Reactor

Figure 1:
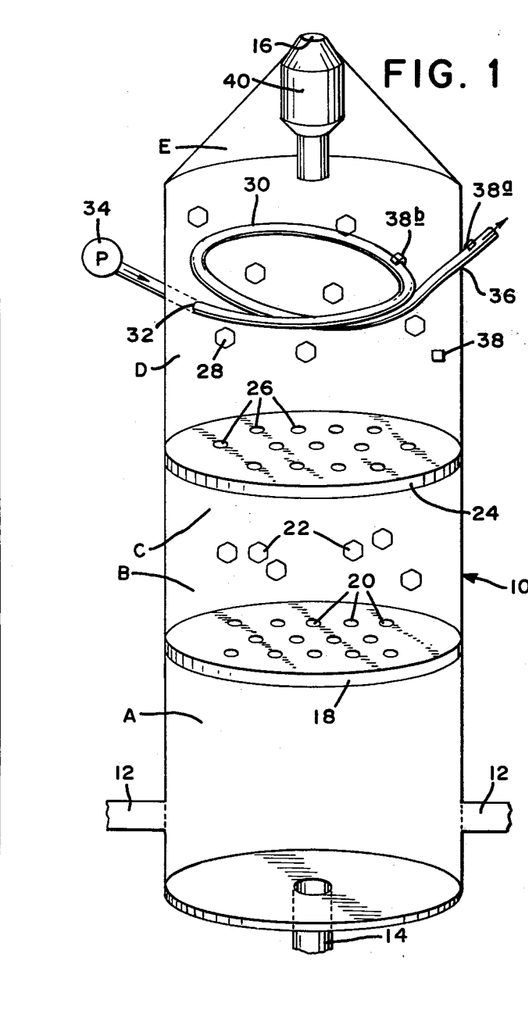
FIG. 1 is an elevational view of a fluid bed reactor according to a first embodiment of the invention.

Referring to FIG. 1, a simple reactor is shown with a large reactor housing 10 having near its lower end reactant inlets 12 and fluidizing gas inlet 14. In some devices the fluidizing gas passes through an inlet 12 with reactants. At its upper end is an outlet 16. The exterior connections to the inlets and outlet will vary of course, depending on the chemical reaction or other process occurring in the reactor, and these connections are not shown since they would be well known in the art.

A short distance above the inlets 12 and 14 is a first or lower grate 18 provided with holes or apertures 20 therethrough.

It should be appreciated that the lower grate may conveniently be sintered to provide microscopic apertures for the upward flow of fluidizing gas and reactants. Such sintered grates are widely available from various commercial sources and methods for their manufacture are well-known in the art. Any lower grate with apertures smaller than the particles would be suitable, except that the number of apertures and thickness of the plate would be adjusted to ensure that fluidized beds are formed above both grates, as discussed below, at a suitable flow rate. Tuyeres and other similar devices well known in the art as being generally equivalent to grates (and preferred for certain applications) may be used. However, for purposes of clarity a grate with visible apertures is shown.

Above the first grate are particles 22 which can be catalytic particles in many reactors. In order to prevent a loss of particles 22, the holes 20 will be smaller in "effective diameter" as defined above than the diameter of all or almost all of the particles 22. Of course, it will be appreciated that apertures 20 may have tortuous paths through the grate 18, or may be covered by other structures, giving them an effective diameter sufficiently small even though the path has a larger diameter at each individual point.

Spaced above the first grate 18 at distance greater than the height of the first fluidized bed, as described below, is an upper second grate 24. It has apertures 26 passing from its bottom to its top. Above the second grate 24 are particles 28 which may be any material, but are preferably of the same composition as the particles 22. In this embodiment, the holes 26 have an actual or effective diameter smaller than the diameter of the particles 28. The second grate 24 could be a tuyere or other device (as, for example, the device illustrated in FIG. 6) which has a large effective diameter from a fluid flow standpoint, but which does not permit backflow of particles. Such designs are well known in the art. Sintered grates may also be used for the second grate 24.

Spaced above the second grate 24 is a cooling coil 30 communicating with an inlet 32 and an outlet 36 to the exterior of the housing 10 of the reactor. A pump 34 is located in the supply to the inlet 32 and is controlled, by connections not shown, by one of the thermostats 38, 38a and 38b located, respectively, on the reactor wall 10 or in the second bed above the second grate 24, in the line leading from the outlet 36 and in the coil 30. For example, the pump 34 may be activated when all three thermostats detect temperatures in excess of preset amounts, or can be controlled by only one or two of the thermostats.

Above the cooling coil 30 and connecting to the outlet 16 is a conventional cyclone 40 as known in the art, which separates small solid particles or "fines" from the fluid flow through the outlet 16. As discussed below, the cyclone used may be of smaller capacity than would be used in a conventional fluid bed reactor of the same size and for the same reaction.

Operation of the Simple Reactor

The reactor 10 is actived by adjusting the flow of fluidizing gas, such as nitrogen, from inlet 14 until the particles 22 above the first grate 18 are fluidized as well known in the art, and also until the particles 28 above the second grate 24 are fluidized. It will be appreciated that amounts of particles 22 and 28, or the number of apertures 20 and 26 can be adjusted to insure that both groups of particles will be fluidized at about the same flow rate through the inlet 14. A first fluidized bed of particles 22 will form above the first grate 18 in the region designated B and a second fluidized bed of particles 28 will form above the second grate 24 in a region designated D.

Assuming the chemical reaction to be a catalytic one, the flow of reactants from inlet 12 will then be started at whatever rates are desired for the reaction. The rate of flow of fluidizing gas can be adjusted downward when reactants are introduced to maintain a relatively constant overall gas flow rate.

For many reactions, the reactants may be preheated before introduction through the inlets 12, and the mixing region A below the first grate 18 may be externally heated, although this is not illustrated. The mixed reactants and fluidizing gas pass upward through the apertures 20 in the first grate 18 and contact the particles 22 which are catalytic particles. The desired reaction occurs in zone B for the desired contact time which can be computed as the average residence time of a small unit of reactants in zone B. The effluent from zone B, now generally converted to products or by-products, quickly traverses zone C and passes upward through the holes 26 in the second grate 24.

In many chemical reactions for which the present invention is particularly suited, the reaction zone B is exothermic. Whether or not exothermic, the reaction in zone B will necessarily occur at an elevated temperature, generally above about 300° C. and often between about 350° C. and about 700° C. However, the apparatus and method of the present invention also encompass even higher reaction temperatures wherein the effluent from zone B is at temperatures above about 700° C.

A cooling system of some conventional type may be provided in zone B to withdraw heat at the elevated temperature, as for example between about 350° and 700° C. Such systems, particularly using molten salts as the coolant, are well known and frequently employed to produce high pressure steam.

The effluent may contain acids and other corrosive materials, as well as water vapor, such that the effluent at the temperature found in zone D would be highly corrosive. Expensive corrosion-proof liners would be required throughout if the effluent were immediately passed through a cyclone to remove fines from the particles 22. Excessively low temperatures, on the other hand, would cause condensation of the water vapor, which would dissolve the acids and again make them more corrosive. A method is required to cool the effluent to a controlled intermediate temperature with minimum contact between the hot effluent and reactor surfaces.

The effluent, after passing through the upper grate 24, contacts the fluidized particles 28 which occupy the area designated zone D. Because, as described below, the particles 28 are kept at a uniform intermediate temperature such as between about 150° C. and about 250° C., the effluent will be quickly cooled to that temperature. This rapid cooling can be accounted for by the very high surface area of the particles 28.

Because the particles 28 are fluidized, they will transfer the excess heat received from the effluent one-to-another until the heat is transferred from the particles 28 to the cooling coils 30. Note that the coil 30 is not contacted by hot, corrosive effluent gases, especially if it is above the lower end of zone D, but instead is contacted by less hot particles 28 which, through rapid heat transfer, will remain only slightly warmer than the coolant inside the coil 30. The pump 34, responsive to excessive temperatures in zone D, will increase the flow of coolant and thus the rate of heat transfer if the particles 28 become hotter than desired.

The effluent from zone D is cooler, and thus less corrosive than the effluent from zone B. Most fines of the particles 22, or elutreated volatile components thereof, that traverse the second grate 24 will be trapped in zone D as the volume of flow decreased because of cooling. The temperature drop will cause condensation of volatiles and the decreased flow rate will cause capture of fines. Operating at a lower volume and temperature, and with less remaining fines, the cyclone 40 can then strip the effluent of almost all remaining solid particles before the effluent passes through outlet 16 for further processing.

Multi-Tube Reactor

Figure 2:
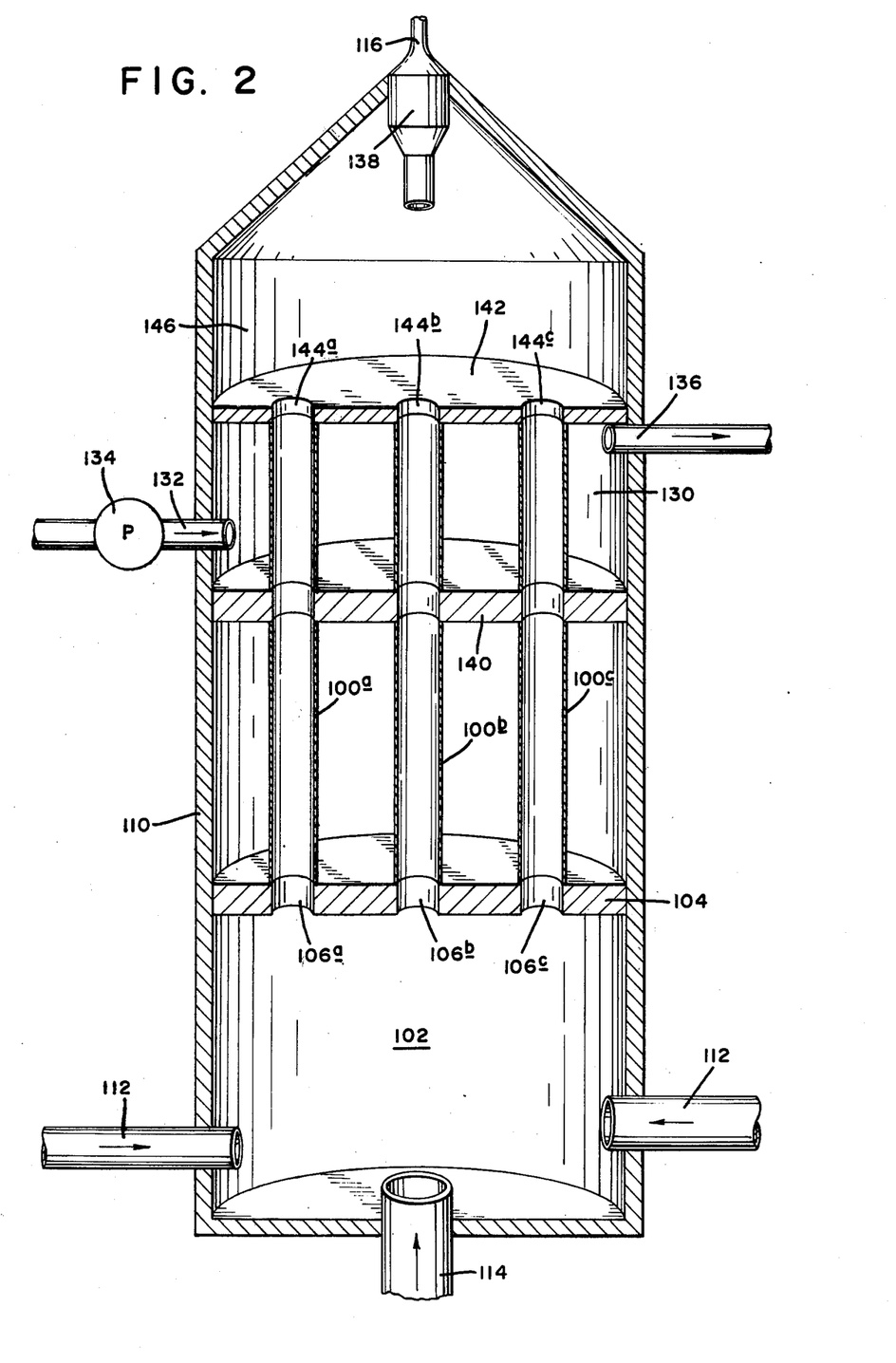
FIG. 2 is an elevational view of a multi-tube fluid bed reactor according to a second embodiment of the invention.

Referring to FIG. 2, a multi-tube reactor is shown with a cylindrical housing 110, in which are supported a series of cylindrical tubes, of which three 100a, 100b, and 100c are illustated. Each tube 100a–c has a longitudinal axis parallel to that of the housing 110. The lower portion of the reactor is a single mixing zone 102 with fluidizing gas inlet 114 and reactant inlets 112. At the top of this mixing zone 102 is a wall 104 extending transversely to the longitudinal axis of the housing 100 and blocking the interior of the housing. Each tube 100a–c has at its lower end an inlet 100a–c, respectively, that traverses the wall 104 and the tubes 100a–c extend upwardly therefrom. At an intermediate height in the housing 110 is a second wall 140, extending in a plane transversed to the longitudinal axis of the housing 110 and the tubes 100a–c, and surrounding the tubes. Higher in the housing 110 is a third wall 142 extending in another plane transverse to the longitudinal axis of the housing 110 and the tubes 100a–c. The tubes are snuggly fitted into holes through walls 140 and 142, with the walls 140 and 142 otherwise blocking the interior of the housing 110. The top ends 144a–c of the tubes 100a–c are conveniently aligned with the top of the upper wall 142.

Thus, an enclosed space 130 is formed by the housing 110, the walls 140 and 142 and the tubes 100a–c, which is inside the the housing 110 but outside the tubes 100a–c. A coolant inlet 132 with a pump 134 communicates with a lower portion of the space 130 through the housing 110, and a cooling outlet 136 communicates with the space 130 through the housing 110 above and generally opposite the inlet 132.

Another space 146 is formed within the top portion of the housing 110 above the upper wall 142. A cyclone 138 is located in the top of the space 146 and extends through the outlet 116 at the top of the housing 110.

Figures 3, 5, 6, 7:
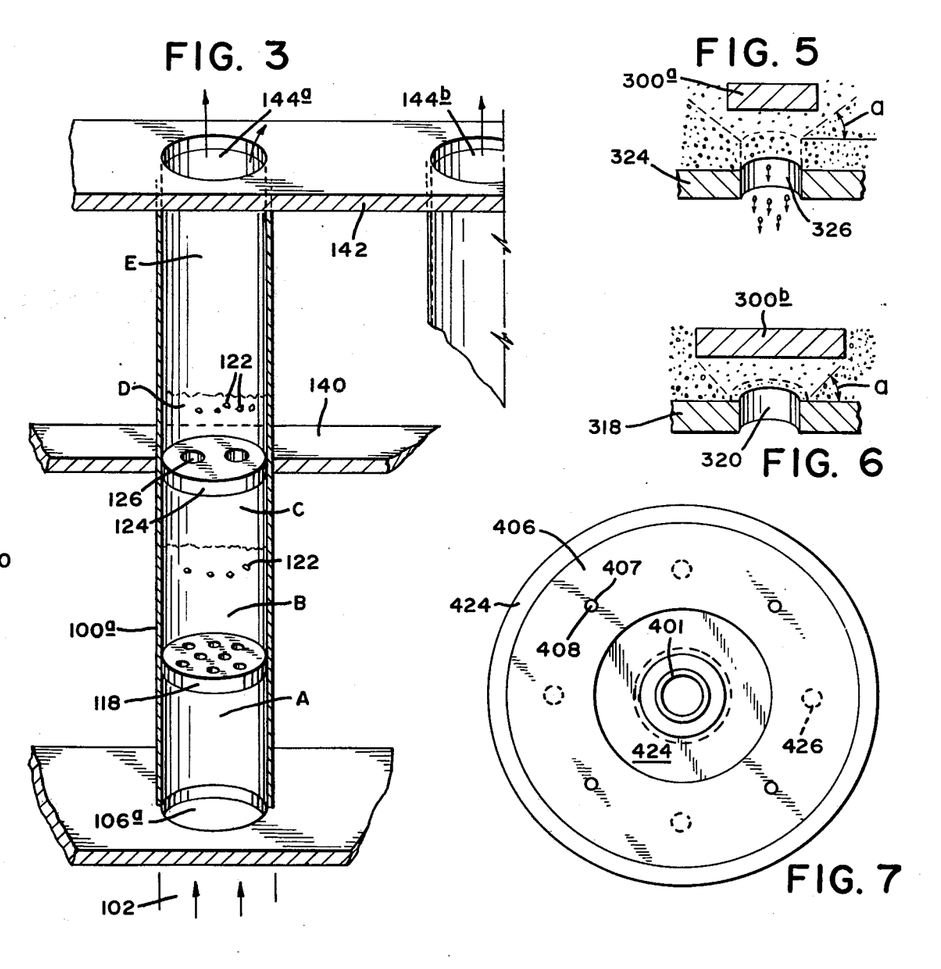
FIG. 3 is an enlarged view of one tube of the reactor of FIG. 2.
FIG. 5 is an enlarged elevational view of an upper grate usable in the present invention.
FIG. 6 is a view similar to FIG. 5 of a lower grate usable in the present invention.
FIG. 7 is an enlarged plan view of an upper grate usable in the present invention.

The detail of one tube, 100a, and surrounding structures are illustrated in FIG. 3. Each other tube, 100b, and c, is identical. Above its inlet 106a is a first or lower grate or support 118 of sintered metal. This plate could be in any form such as a perforated plate, a double effect plate or the design shown in FIG. 7. Some particles 122 are above the first grate 18 and, as described below, form a first fluidized bed in the region designated B. Spaced above the first grate 18 by a distance greater than the anticipated height of the first fluid bed is a second or upper grate or support 124 with large apertures (or a single aperture) greater in diameter than the particles 122. As discussed below, upon fluidization, a second fluid bed forms above the second grate in the region designated D.

The second grate 126 is at about the same height as the wall 140 such that the region D will generally correspond to at least the bottom of the space 130 outside the tubes 100a–c but inside the housing 110.

Operation of the Multi-Tube Reactor

Referring to FIGS. 2 and 3, the multi-tube reactor is started with substantially all the particles 122 resting on top of the lower grate 118 to a level below or at or above the upper grate 124. As the flow of fluidizing fluid from the inlet 114 is increased, movement and then fluidization of the particles 122 begins above the lower grate 118 in zone B. As the flow of fluidizing gas is increased beyond the point of minimum fluidization, some particles 122 are carried above zone D through the next zone C below the second grate 124 and through the large holes 126 in the second grate 124. So long as the flow rate is not increased excessively, almost all of the particles 122 remain in zone D above the second grate 124 and few traverse the next zone E and pass through the outlet 144a of the tube 100a. Of course, each tube 100a–c undergoes the same process simultaneously because of the common feed of fluidizing gases from mixing zone 102.

So long as the flow of fluidizing gas, and later reactants as well, is kept substantially constant, an equilibrium is established and maintained between a first fluidized bed in zone B above the first grate 118 and a second fluidized bed in zone D above the second grate 124. Some particles continue to traverse zone C and the second grate 124 through the large holes 126 in both directions, but the net flow is nil or negligible and the actual flow in each direction is a relatively small (and adjustable) proportion of the total particles 122. Careful adjustment of the size of the holes 126 is desirable to provide a ratio of heights of the two fluid beds. As shown in Examples 1–3 below, a variety of grates 124 may be used for a particular sized tube 100a and particles 122, although a ratio of effective hole diameter to particle diameter of greater than about 2 is required to avoid blockage.

Once fluidization and equilibrium are achieved, the reactants, heated if desired, are fed into the mixing zone 102 from the inlets 112. They will pass upward through each tube 100a–c, through zone A and through the lower grate 118 into zone B in which the particles 122, which may be catalytic, are fluidized. The desired reaction occurs in this lower fluidized bed at the reaction temperature. If the reaction is highly exothermic, heat may be withdrawn as by a high temperature coolant system in the space surrounding the zone B of each tube, not shown, but substantially similar to the space 130 described above.

The effluent from the first fluidized bed traverses zone C and the second grate 124 through holes 126. The effluent is rapidly cooled by contact with the particles 122 in the second fluidized bed in zone D above the second grate 124. The heat so transferred is transferred among the fluidized particles and then through zone D to the walls of the tube 100a. Coolant fluid in the space 130 around the tubes 100a–c withdraws this heat through the walls of the tubes 100a–c. Referring to FIG. 2, the coolant is fed by pump 136 into the space 130 through the coolant inlet 132. Heated or vaporized coolant leaves the space 130 through the coolant outlet 136. Thermostat elements, not shown, in the space 130 detect any rise in temperature to above a preset level, activating the pump 136.

The cooled effluent, stripped of much of the fines and volatile catalyst components, leaves the tubes 100a–c and enters the space 146 before passing out of the housing 110 through the cyclone 138 and outlet 116. Very little solid or condensable material remains for the cyclone 138 to strip. The flow rate beyond the outlets 144a–c of the tubes 110a–c is particularly slowed down because of the temperature drop caused by the second fluidized bed and the coolant flowing through the space 130, and because of the increased cross-section of the space 146 compared to the tubes 100a–c.

The operation of this multi-tube reactor has all of the advantages of a simple reactor system including quenching the reaction, heat recovery if desired, lessened corrosion and lessened loss of volatiles and fines. Additionally, because of the large-holed second grate 124 and the equilibrium established between the two fluid beds, recondensed volatiles will gradually return to the lower, catalytic fluidized bed and will not plug either grate or the cyclone. The interchange of the particles between the two fluidized bed is sufficient to recycle volatiles but insufficient to materially affect the sharp temperature differential.

Of course, many of the above advantages can be obtained using an expanded form of the tube 100a as a simple reactor, and such a reactor is within the scope of the invention. This form of the invention is particularly suited, however, for multi-tube reactors with small diameter tubes where the few large holes or single hole in the second grate will not become blocked. Multi-tube reactors may also be chosen because, as frequently occurs with exothermic reactions, product yields decline with increasing diameters of the reaction vessel. Multi-tube reactors also present the opportunity for holding several zones, including the second fluid bed of zone D, at constant temperature in each tube.

Modified Multi-Tube Reactor

Figures 4, 8:
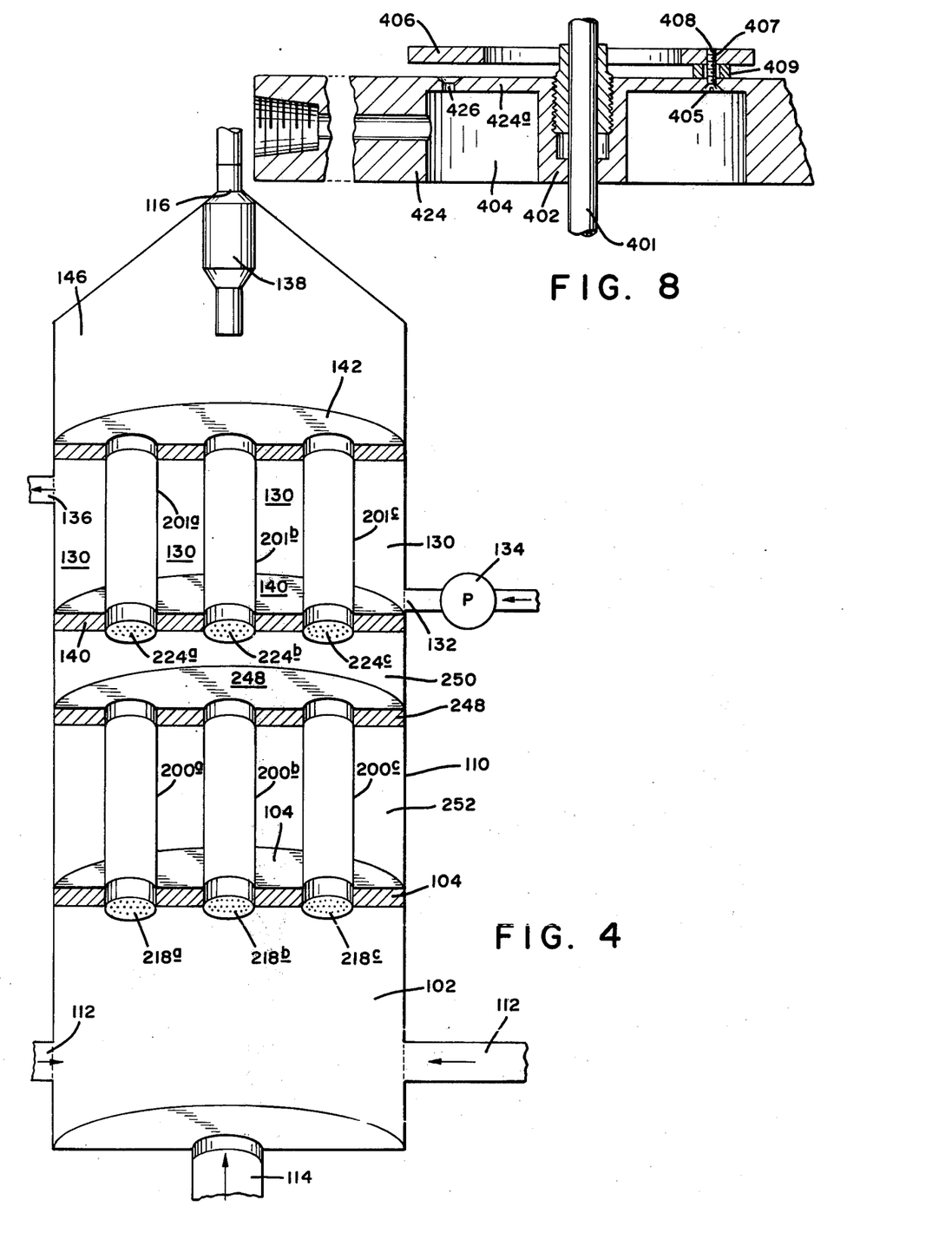
FIG. 4 is an elevated view of a multi-tube fluid bed reactor according to a third embodiment of the invention.
FIG. 8 is further enlarged elevational view of the grate of FIG. 7.

Referring to FIG. 4, a multi-tube reactor is shown, with each similarly numbered element being identical to the corresponding element in the embodiment illustrated in FIG. 3. In general, a housing 100 is provided with a mixing zone 102, fluidizing gas inlet 114, reactant inlet 112, an outlet 116 in which is provided a cyclone 138 and an upper space 146 below the outlet 116. A space 130 defined by an upper wall 142 and another wall 140, corresponding generally to the second fluidized bed, is provided, with coolant circulating in through the space 130 from an inlet 132 (providing with a pump 134) and an outlet 136.

Additionally, the lower plate 104, generally adjacent the first grates 218a–c forms the bottom of a lower space 252 generally adjacent the first fluidized bed. This space 252 is enclosed by the exterior of several short lower tubes of which are illustrated three 200a–c, the lower plate 104 and a middle plate 248 provided at the top of the shortened tubes 200a–c. Another space is thereby provided above the middle plate 248 and below the second grates 244a–c. To provide proper gas flow rates and to maintain the second bed, the grates 224a–c do not permit particle backflow, and thus are designed like grates 24 and not like grates 124a–c. Above this space 250 is the plate 140, which defines the bottom of the space 130. Within the space 130 are upper tubes 201a–c collinear with the lower tubes 200a–c, respectively.

In operation, as before, fluidizing gases, and later also reactants, are passed from the mixing zone 102 through the lower grates 218a–c and through the lower fluidized beds. The effluent now passes out of the tubes 200a-c into the open space 250 before passing upward through the second grates 244a-c and into the upper tubes 200a-c. Within the upper tubes 201a-c are the second fluidized beds, in which the effluent is cooled and quenched before passing beyond the upper plate 142, through the space 146 in the cyclone 138, and out the outlet 116.

The operation of this modified multi-tube reactor is generally the same as of the multi-tube reactor illustrated in FIGS. 2-3, except that no interchange of particles between beds occurs. In this embodiment a space 252 is now provided around the lower tubes 200a-c adjacent the first fluidized bed, to enable a higher temperature coolant to be circulated therethrough to maintain the first fluidized bed at a desired high temperature. The space 250 between the tops of lower tubes 200a-c and the bottom of upper tubes 201a-c provides a region for pressure equalization between the three parallel systems.

Another suitable modification would include moving the upper grates 224a-c to the top ends of the lower tubes 200a-c, parallel to the middle plate 248. A single, large upper fluidized bed could be formed in space 250 upon careful adjustment of the size and number of the apertures 224a-c. Cooling could be effected by withdrawing heat into the space 130 through the plate 140, or to another area of coolant.

Suitable Modified Grates

Examples of other apertures or grates are shown in FIGS. 5 and 6. In FIG. 5 is shown a modified upper grate 324 with an aperture 326 covered by a wide plate 300a. This plate may be ring-shaped to cover a plurality of apertures 326 or ring-shaped with offset holes. The width of the plate 300a is sufficiently small that, as particles pile up on the grate 324, many of them will angle inwardly under the plate 300a and fall downward through the aperture 326. The angle a formed by the particles is the well known "angle of repose" which is dependent on the particle size, shape and composition. Accordingly, many of the particles can easily fall downward through the aperture 326.

In FIG. 6 is shown a modified lower plate 318 in which an aperture 320 is covered by a wider plate 300b. This plate 300b may also be ring-shaped or otherwise designed to cover a plurality of holes 320. With the wider plate 300b, the particles, even when fluidization is stopped, will not fall downward through the hole 320. Instead they will generally pile up around the plate 300b and may angle inwardly at their "angle of repose" a under the plate 300b, but not far enough to fall downward through the hole 320.

Of course, many other designs of grids or plates may be used, with those designs which permit the flow of particles downward being preferred for upper grates 24 or 124.

In FIGS. 7 and 8 is shown, in another preferred form of the invention, a disc-shaped upper grate 424 suitable for the fluid bed reactors of the present invention. A thermowell 401 is provided normal to the disc-shaped grate 424 extending linearly both above and below the grate 424 within a sleeve 402. An annular recess 404 defined by the bottom of the grate 426 surrounds the sleeve 402. Several circumferentially spaced apertures 426 pass through the thin portion 424a of the grate 424 above the annular recess 404. Each aperture 426 is conically countersunk from the top such that its diameter at the top of the portion 424a is about twice its diameter at the bottom of the portion 424a.

Also circumferentially spaced in the thin portion 424a are several helically threaded holes 405 countersunk on the bottom. An annular plate 406 overlaps the grate 424 with its nominal center along the thermowell 401 above the grate 424. Several threaded holes 407 are defined by the annular ring 406 that can be aligned with the threaded holes 405 and joined thereto by bolts 408. A cylindrical spacer or washer 409 is placed around each bolt 408 to fix the spacing between the bottom of the annular ring 400 and the top of the grate 424.

It can be appreciated that, by selecting a bolt 408 and washer 409 of a selected height, the separation of the annular plate 406 off of the grate 424 can be selectively varied. By selecting an annular plate 406 of a selected width, the extent to which the plate 406 extends beyond the apertures 426 radially can be selectively varied.

This design is somewhat less preferred than large-apertured grates (i.e. grates 224 a-c in FIG. 4).

Other suitable modifications may be made in the above embodiments without departing from the scope of the invention. For example, instead of the small holed-grids used for grids 18, 24, 118a, 218a and 124a, or instead of the grid design illustrated in FIG. 7 and 8, a tuyere grid may be used. In such a grid, each aperture includes a vertical hole through the grid within a "bubble-cap" extending above the grid and a connected horizontal hole through the "bubble-cap". Such tuyeres are well-known in the art, finding particular use in the drying of iron ore.

EXAMPLES 1-3

Simulated Two Grid Reactor

A cylindrical, glass simulated reactor having an inside diameter of three inches and a height of twelve feet was fixed with a lower, sintered Inconel grid at the bottom of the cylinder. An apertured upper grid was placed at a height of four feet. A profile thermowell was inserted along the length of the cylinder.

To test the ability of the bed to maintain a temperature differential, a steam coil was placed above the second grid. Particles of aluminum fluoride were added to a height of six feet. In these examples, the second grid contained at least one aperture larger than the particle diameter.

Example 1—¾ inch diameter orifice

Using a second grid with a single orifice of ¾ inch diameter, the simulated reactor was fluidized by a nitrogen flow of 0.6 feet per second (FPS). Two beds formed with a six inch space easily observed between the top of the lower first bed and the bottom of the second grid. With the upper bed heated to 110° C., the lower bed rose in temperature to 75° C. With the nitrogen flow increased to 1.0 FPS, the observed bed temperatures were 114° C. in the upper bed and 72° C. in the lower bed. In each case, the temperature was relatively constant for the entire first, lower bed, rose slightly across the space between the first bed and the second grid, and rose sharply across the second grid. The temperature of the second bed was generally uniform.

EXAMPLE 2 —½ inch diameter orifice

The procedure of Example 1 was repeated with a 3 inch diameter upper grid having a single orifice of ½ inch diameter. At a nitrogen flow rate of 0.6 FPS, a temperature differential was established with the first, lower bed at 38° C. and the second, upper bed at 100° C.

Example 3 —three ⅜ inch diameter orifices

The procedure of Example 1 was repeated with a 3 inch diameter upper grid having three orifices, each with a ⅜ inch diameter. A temperature differential was established with the lower bed at 30° C. and the upper bed at 100° C.

It should be appreciated that these simulated reactor tests provide an excellent mode of testing for the proper upper grid using the lower grid, particles and gas flow rates desired for actual reactor operation. The ability to maintain a temperature differential between a heated upper bed and a cool lower bed correlates very well with the ability to maintain a cooler upper quenching bed above a hot lower reaction bed.

EXAMPLE 4

The 3 inch diameter grid with a ½ inch diameter orifice of Example 2 was fitted at a height of 4 feet in a 4 inch outside diameter (three inch ID) insulated Inconel reactor. The insulation was removed above the 4 foot level and a steam cooling coil placed in this portion of reactor. An actual oxychlorofluorination reaction was conducted in the lower bed, with hydrogen fluoride, oxygen and methane reactants being converted to chlorofluorinated methanes and water by catalyst particles. As described in the pending application of Henry R. Nychka et al., Ser. No. 642,874, filed Dec. 22, 1975, now U.S. Pat. No. 4,052,470, issued Oct. 4, 1977, this reaction involves certain critical amounts of the various reactants and fluidized catalyst particles of aluminum fluoride coated with a copper chloride potassium chloride eutectic.

To avoid clogging of catalyst particles, fluidization was achieved at room temperature with a 0.5 FPS nitrogen flow. Subsequently, reactant gases were added, heated to about 400° C. The lower, reaction bed had a height of about 3½ feet. In two runs, good separation was achieved with the lower, reaction bed at 460°–490° C. and the upper, cooling bed at 250°–290° C. No plugging occurred.

EXAMPLES 5–6

A 3 inch inside diameter reactor with five Inconel sections, each of 47¾ inches, was tested with two fluidized beds. A sintered Inconel lower grid was located at the bottom of the reactor. A second grid as shown in FIGS. 7 and 8 with four #41 holes in a double Inconel 600 plate was located between the third and fourth section and thus at a height of just under 12 feet. The lower three and top sections were insulated, but the insulation was removed from the fourth section. Upon fluidization, the lower fluidized bed was about 72 inches high in Example 5 the run was for 25¾ hours. In Example 6, the second grid plugged at 9½ hours and was shut down.

The feeds in Example 5 were, in grams per hour HF 273.6, HCl 1138.8 $O_2$ 706.9, $CCl_2F_2$ 490.0, $CH_2Cl_2$ 703.8, $CH_4$ 117.8, and $N_2$ 1175.0. A pressure drop was observed which gradually increased to pressures of 50 psig entering the unit and 20 psig above the second bed. The pressure at the sample point below the second bed was 44 psig.

During the first run, the HCl, HF and $N_2$ feeds were shut off between 10 and 13 hours during which time the pressure drop disappeared. The pressure drop also appeared in Example 6 with the pressure at the inlet gradually increasing from 25 psig to 45 psig. This pressure drop was accompanied by a decrease in carbon utilization.

The pressure drop was believed to be caused by plugging of the second grid. After shutdown of the run of Example 5, a grey plug was found in and below the second grid with amounts of copper, potassium, iron, chromium and nickel indicative of depositing of both volatiles from the catalyst particles and corrosion products.

Selected temperature readings from Examples 5 and 6 are shown in Table I.

TABLE I

| | | Temperature °C. | | | |
|---|---|---|---|---|---|
| | | Example 5 | | | Example 6 |
| Height | 9 hours | 15½ hours | | 19½ hours | 6½ hours |
| 0 | 200 | 60 | 80 | 220 | 60 |
| 1' | 445 | 60 | 450 | 339 | 50 |
| 2' | 453 | 80 | 456 | 435 | 50 |
| 3' | 460 | 450 | 455 | 436 | 461 |
| 4' | 460 | 456 | 456 | 435 | 468 |
| 5' | 461 | 455 | 459 | 439 | 462 |
| 6' | 463 | 456 | 460 | 442 | 462 |
| 7' | 468 | 459 | 460 | 444 | 462 |
| 8' | 476 | 460 | 461 | 451 | 465 |
| 9' | 480 | 460 | 463 | 457 | 460 |
| 10' | 463 | 461 | 453 | 451 | 450 |
| 10'6" | 380 | 462 | 393 | 410 | — |
| 11' | 270 | 453 | 300 | 280 | 435 |
| 11'6" | 255 | 453 | 275 | 265 | — |
| 12' | 258 | 453 | 263 | 253 | 412 |
| 13' | 248 | — | 260 | 253 | 260 |
| 14' | 220 | — | 245 | 240 | 255 |
| 15' | 210 | — | 260 | — | 250 |

Average gas chromatography readings taken of samples through each run are shown in Table II. They demonstrate a low degree of back or side reaction in the second bed.

TABLE II

| | Weight % (normalized to disregard nitrogen) | |
|---|---|---|
| Component | Below Second Grid | Above Second Bed |
| $O_2$ | 8.76 | 8.57 |
| $CH_4$ | 0.67 | 0.60 |
| $CO_2$ | 7.01 | 8.89 |
| $CClF_3$ | 0.0 | 0.05 |
| $CCl_2F_2$ | 24.10 | 24.00 |
| $CH_3Cl$ | 0.05 | 0.0 |
| $CHCl_2F$ | 0.21 | 0.12 |
| $CCl_3F$ | 27.62 | 27.53 |
| $CH_2Cl_2$ | 0.38 | 0.28 |
| $CHCl_3$ | 4.60 | 4.07 |
| $CCl_4$ | 26.58 | 25.89 |

EXAMPLE 7—Corrosion Testing

During the run of Example 6, steel and Inconel tubes were suspended in the first bed, above the first bed, in the second bed and above the second bed. Based upon material loss, corrosion rates calculated for a rate based upon total time of fluidization and also upon the time the first bed was above 400° C. (reaction time). These rates are shown in Table III with the rates based upon reaction time in parentheses.

TABLE III

| Sample Material | Location | Corrosion Rate (mils/year) |
|---|---|---|
| Inconel 600* | 1st Bed | 83.2 (193.3) |
| Steel 285C** | Above 1st Bed | 304.8 (482.0) |
| Steel 285C** | In 2nd Bed | 70.2 (111.1) |

TABLE III-continued

| Sample Material | Location | Corrosion Rate (mils/year) |
| --- | --- | --- |
| Steel 285C** | Above 2nd Bed | 150.7 (238.3) |
| Inconel 600 | Above 1st Bed | 68.8 (108.8) |
|  | In 2nd Bed | 2.5 (4.5) |
|  | Above 2nd Bed | 23.1 (36.6) |

*A commercially available product of the International Nickel Company composed of about 76 weight % nickel, 7.2 weight % iron, 15.8 weight % chromium and trace materials.
**A standard grade of carbon steel.

This example shows that the gases in and above the second bed are less corrosive than the effluent from the first, reaction bed.

We claim:

1. A fluid bed reactor comprising:
   (a) a housing having an inlet and an outlet;
   (b) a plurality of parallel tubes within said housing, each tube having an inlet adjacent the housing inlet and an outlet adjacent the housing outlet;
   (c) a first grid within each said tube adjacent said tube inlet;
   (d) a first fluidized bed of particles within each said tube supported on said first grid;
   (e) a second grid within each said tube between said first grid and said tube outlet;
   (f) a second fluidized bed of particles within each said tube between said second grid and said tube outlet;
   (g) heat exchange means for withdrawing heat from each said second fluidized bed of particles; each said first fluidized bed of particles being at a temperature greater than the minimum reaction temperature of a selected chemical reaction and each said second fluidized bed of particles being at a temperature less than said minimum reaction temperature.

2. A fluid bed reactor as claimed in claim 1 wherein said second grid has an aperture larger in effective diameter than the particles of said first and second fluidized bed of particles, whereby said particles can traverse said second grid, said second grid and aperture being dimensioned such that under reaction flow rates of the fluid, an equilibrium of particles will be established between said first and second beds across said second grid sufficient to permit a selected interchange of particles across said second grid, but insufficient to reduce the temperature differential between said first and second fluidized beds beyond a selected amount.

3. A fluid bed reactor as claimed in claim 2 wherein said aperture is about 30 to about 200 times as large in diameter as the average diameter of the particles of said first and second fluidized beds.

* * * * *